US007440856B2

(12) United States Patent
Pardo et al.

(10) Patent No.: US 7,440,856 B2
(45) Date of Patent: Oct. 21, 2008

(54) SYSTEM AND METHOD FOR DETERMINING CLINICAL EQUIVALENCE OF TEST METHODS

(75) Inventors: Scott A. Pardo, Wesley Hills, NY (US); Karen J. Byron, Ringwood, NJ (US); Valerie Bush, Wanaque, NJ (US); Julie Berube, Ringwood, NJ (US); Shankang Qu, Fair Lawn, NJ (US); Henry T. Davis, Kinnelon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 718 days.

(21) Appl. No.: 10/096,102

(22) Filed: Mar. 13, 2002

(65) Prior Publication Data

US 2003/0172712 A1 Sep. 18, 2003

(51) Int. Cl.
*G06F 19/00* (2006.01)
(52) U.S. Cl. ...................................................... 702/19
(58) Field of Classification Search .................... 702/19, 702/31, 108, 119–123, 179–183; 600/544, 600/559; 128/898
See application file for complete search history.

(56) References Cited

U.S. PATENT DOCUMENTS

| | | | | |
|---|---|---|---|---|
| 6,041,788 A | * | 3/2000 | Shen | 128/898 |
| 6,434,511 B1 | * | 8/2002 | Stein et al. | 702/179 |
| 6,556,951 B1 | * | 4/2003 | Deleo et al. | 702/183 |
| 6,567,750 B1 | * | 5/2003 | Nadon et al. | 702/19 |
| 6,678,669 B2 | * | 1/2004 | Lapointe et al. | 706/15 |
| 6,847,976 B1 | * | 1/2005 | Peace | 707/102 |
| 6,876,929 B2 | * | 4/2005 | Nadon et al. | 702/19 |
| 7,050,933 B2 | * | 5/2006 | Parvin et al. | 702/179 |
| 7,133,715 B1 | * | 11/2006 | Smits et al. | 600/544 |
| 2003/0003450 A1 | * | 1/2003 | Hubbell | 435/6 |

OTHER PUBLICATIONS

Vacek P M: "The Effect of Conditional Dependence on the Evaluation of Diagnositc Tests"; Biometrics, Biometric Society, Raleigh, NC, U.S.; Dec. 1985; pp. 959-968; vol. 41, No. 4.

(Continued)

*Primary Examiner*—Edward Raymond
*Assistant Examiner*—Mohamed Charioui
(74) *Attorney, Agent, or Firm*—Mark J. Schildkraut

(57) ABSTRACT

A system, method and computer readable medium of instructions are provided which are useful for determining whether an evaluation testing method or device is clinically equivalent to a reference testing method or device. The report can include a modified mean difference plot, a variability chart, confidence intervals for bias and a plot of the intervals. A graphical user interface is provided to allow data associated with the reference and evaluation methods or devices to be identified. A level of variance in the reference method is determined. An observed bias between the evaluation methods or devices and the reference methods or devices is calculated. A confidence interval for the bias is calculated. The biases between the evaluation methods or devices and reference method or device is compared relative to the level of variance in the reference method, and a report is generated including a conclusion about whether the evaluation methods or devices are clinically equivalent to the reference method or device.

23 Claims, 8 Drawing Sheets

OTHER PUBLICATIONS

Fulford K M et al: "Reference Preparation to Standardize Results of Serological Tests for Rheumatoid Factor"; Journal of Clinical Microbiology; 1978; pp. 434-441; vol. 7,No. 5.

G. Hripcsak et al: "Reference Standards, Judges, and Comparison Subjects: Roles for Experts in Evaluating System Performance'"; Journal of the American Medical Informatics Association, USA; Jan. 2002; pp. 1-15; vol. 9, No. 1.

Long T: "Statistical Power in the Detection of Matrix Effects"; Archives of Pathology, American Medical Association, Chicago, IL, US; Apr. 1993; pp. 387-392; vol. 117, No. 4.

London L et al: "Repeatability and Validity of a Field Kit for Estimation of Cholinesterase in Whole Blood"; Occupational and Environmental Medicine, Appleton & Lange, Stamford, CT, US; Jan. 1995; pp. 57-64; vol. 52, No. 1.

Ross J W et al: "The Accuracy of Laboratory Measurements in Clinical Chemistry A Study of 11 Routine Chemistry Analytes in the College of American Pathologists Survey with Fresh Frozen Serum, Definitive Methods, and Reference Methods"; Archives of Pathology, American Medical Assoc., Chicago, IL, US; Jul. 1998; pp. 587-608; vol. 122, No. 7.

Kjems U et al: "The Quantitative Evaluation of Functional Neuroimaging Experiments: The NPAIRS Data Analysis Framework"; Neuroimage; Apr. 2002; pp. 747-771; vol. 15, No. 4.

* cited by examiner

Exp Name: AST

Study Information:
   30 donors
   2 Serum observations per donor
   1 SST observation per donor 0 missing Serum observations
   1 missing SST observation
   29 comparisons
   90 expected observations
   89 actual observations Regression Information:
   Intercept = 1.2 (-0.16, 2.55)
   Slope = 0.939 (0.873, 1.01)
   R squared = 96.9%

Simultaneous Test of Intercept and Slope:
   p-value = 6.99%
   Accept Ideal Line Hypothesis

SYSTEM AND METHOD FOR DETERMINING CLINICAL EQUIVALENCE OF TEST METHODS

FIELD OF THE INVENTION

The present invention relates to a system and method for evaluating testing methods. In particular, the present invention relates to a system and method for comparing two or more testing methods, systems, or products. The invention is particularly useful in the medical testing field, to determine if the methods, and any results obtained therefrom, are clinically equivalent. However, the invention could easily be applied to any laboratory situation in which measurements made under different conditions are compared in order to determine whether the different conditions alter the results in a significant way.

BACKGROUND OF THE INVENTION

Clinical laboratories perform tests for doctors and healthcare professionals. The laboratories perform tests on human blood, urine, plasma, serum or other body fluids in order to measure chemical or physical properties of the specimens. The results of these tests are used by doctors and healthcare professionals to make clinical decisions related to patient care and treatment. Because results are used to make clinical decisions for patient care, dependable test results are of the utmost importance.

Clinical laboratories purchase supplies and products in order to perform these tests. For example, blood collection tubes, needles, diagnostic instruments, chemical reagents and other supplies are used during testing, and therefore must be periodically replenished. From time to time, some element of a testing procedure may change for a variety of reasons. For example, a new blood collection tube type may replace an older version, new blood collection tubes may include a new additive, or a new blood collection tube could be made of plastic rather than glass. Chemical reagents may be ordered from a different supplier, or even a new batch of reagents could be considered a change in the testing procedure. Furthermore, the diagnostic instruments used to perform the testing themselves may change. Newer models may replace older testing equipment. Also, hardware, software and firmware updates may be applied to the equipment.

Of course, the above-described list of variables in testing procedures is merely exemplary, and the list of possible variables is endless. It is important to recognize, however, that any change in testing procedure can potentially affect test results. Therefore, because the accuracy of test results is so important, there is a need for a way to gather and analyze empirical data to show that the testing procedure using the new method, device or system does not significantly affect the testing results.

There is certain degree of variability in any testing procedure. By analyzing test data, it is possible to measure the variability in test results. In addition, a new test procedure or method may give results that are on the average different from a "reference" test procedure. This average difference is called bias. If the bias between a new test procedure and a reference method is small enough, and the variability in the results using the new procedure is no greater than the variability of the old test procedure, the new test procedure can be considered clinically equivalent to the old test procedure. There is presently specialty software on the market for evaluating and validating testing methods. However, the existing software products fall short in several respects.

Currently, most if not all clinical laboratories rely on a statistical technique called linear regression to compare testing methods, systems or products. The linear regression analysis is almost always accompanied by a graphical representation called a scatter diagram. In a scatter diagram, the results from one method, system or product are plotted against the results from the "reference" method or system on a chart and linear regression analysis is used to determine a best-fit line on the chart to represent the data points. A perfect result on a scatter diagram would be a line having a slope of one and a vertical axis intercept of zero. Unfortunately, the degree to which the best-fit line fits the observed data depends on the number and frequency distribution of data values used. Therefore, the quality of the best-fit line for its accuracy and usefulness may be manipulated by selecting individuals at either end of some analytic spectrum and including their results in the data. Thus, while scatter diagrams and linear regressions may be helpful in determining the similarity of results between a reference and evaluation method, system or product, they are not sufficient.

A commonly used quantity calculated by existing software packages is called $R^2$, sometimes referred to as the coefficient of determination. $R^2$ can have a value between 0 and 1, and represents the degree to which a straight line fits the data, relative to the total variability observed. A value of 1 indicates that all the points fit exactly on the same line. Often, $R^2$ is seen as a measure of equivalence between the reference and evaluation methods, systems or products. Unfortunately, $R^2$ is susceptible to a priori manipulation. For example, suppose two tests designed to measure cholesterol values in human blood are to be compared. Some patients may have very high cholesterol values while others may have very low cholesterol values. If two methods for measuring cholesterol are being compared using a linear regression best-fit line, then a high value of $R^2$ may be falsely interpreted as indicating equivalence of the two methods. In fact, the high value of $R^2$ is may only be indicating that there are patients included in the study whose cholesterol values are at the high and low ends of the human spectrum. Because $R^2$ is susceptible to manipulation, it is not a good quantity to be depended upon for measuring the clinical equivalence of a new test method.

Still another disadvantage of current test validation methods, is that they typically validate only a single test method at a time. Thus, for a testing device which is capable of testing 30 separate analytes, using previous testing validation methods 30 separate validations will have to be performed. Accordingly, it would be advantageous to have a single software package which could validate all 30 testing methods at one time.

Therefore, there is a need for a test method validation system which reliably measures the accuracy and precision of a new testing method, determines whether the new testing method is clinically equivalent to a previous testing method, and is capable of validating a plurality of test methods at one time.

SUMMARY OF THE INVENTION

The above needs are addressed and other advantages are realized in a method and system according to an embodiment of the present invention. The method according to an embodiment of the present invention comprises the steps of determining a level of variance in a reference method, determining the average difference in results of the reference and evaluation testing methods, and comparing the average difference between the two methods relative to the level of variability of the reference, and based on the comparison, generating a report indicating whether the evaluation testing method is clinically equivalent to the reference method. The acceptable difference between results of the reference and evaluation testing methods can be calculated by comparing two sets of reference test data associated with the reference method. Alternatively, the acceptable difference can be defined by the user. The report comprises a plot of confidence intervals for bias, modified mean difference plot, a variability chart having a first axis representing accuracy and a second axis representing precision, a scatter diagram with best-fit regression line and associated statistics, as well as a conclusion as to whether the evaluation testing method is clinically equivalent to the reference method. The report also contains a summary statistics table, a table of the bias confidence intervals, the limits on allowable bias as optionally input by the user, and an Appendix containing all the input data. Finally, in the method according to an embodiment of the present invention, data associated with the reference testing method and the evaluation testing method can be conveniently identified by the user through a graphical user interface.

BRIEF DESCRIPTION OF THE DRAWINGS

The invention will be better understood with reference to the following description and the attached drawings, in which.

In the drawing figures, it will be understood that like numerals refer to like structures and method steps.

DETAILED DESCRIPTION OF THE INVENTION

Figure 1:
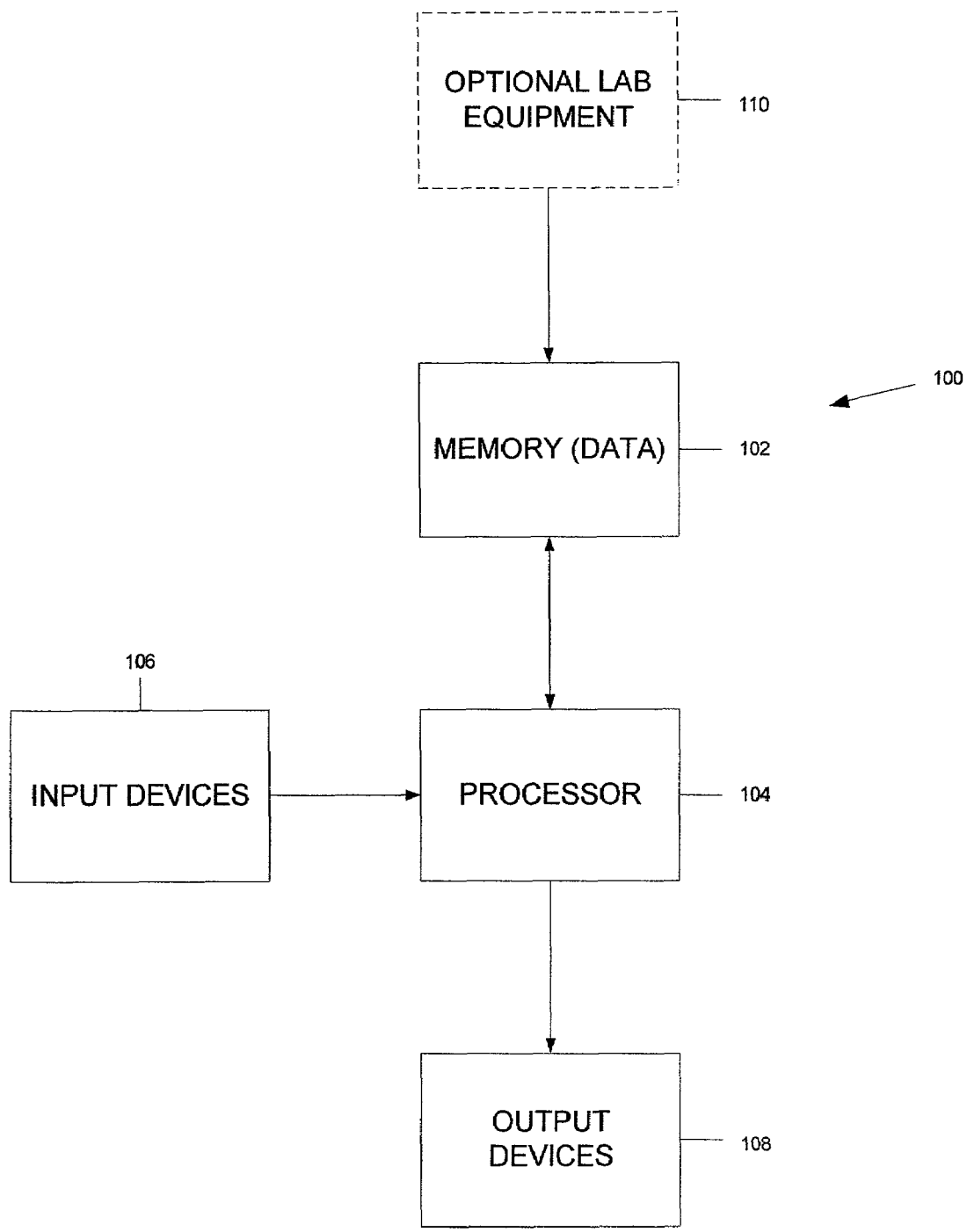
FIG. 1 is a block diagram of a system according to an embodiment of the present invention.

A block diagram of an exemplary system 100 in accordance with an embodiment of the present invention is shown in FIG. 1. The system preferably includes a memory 102 for storing test data. The memory 102 is accessible from a processor 104. Processor 104 receives inputs from input devices 106, such as a keyboard and mouse. Processor 104 also produces outputs which are displayed on an output device 108, which can be a monitor or printer, for instance. The memory 102 preferably stores test data to be evaluated, but may store other information, such as program instructions for executing a program in accordance with an embodiment of the present invention. Data can be entered into memory 102 through user input devices 106, or alternatively, optional lab equipment 110 can automatically store test results.

Processor 104 executes a set of machine instructions adapted to evaluate the test data stored in memory 102. The test data relates to test results obtained using various testing methods on a common set of donors, as will be explained in greater detail below. The data includes at least one and preferably two results per subject using the reference (control) methods, and at least one result for each evaluation method. Processor 104 is adapted to perform a series of calculations which determine if the evaluation test methods are clinically equivalent to the reference method or methods. The calculations and steps performed by the processor to make this determination will be described in greater detail below.

An exemplary set of data associated with two reference test method results and one result from each of two evaluation test methods per subject is reproduced in Appendix A. These data, as shown, are preferably stored in a spreadsheet program, such as Microsoft® Excel. As shown, the data are stored in cells of a table identified by columns and rows. Rows 2-4 of the exemplary table contain information about the test, including the test name, the units appropriate to the results of each test, and user-defined limits of equivalence (acceptable bias) for each test. As shown the limits can be expressed in exact quantities, such as 2 mmol/L for Sodium, or in percentages, such as 10% for AST.

As further shown in the table of Appendix A, Row 6 contains labels for f each of the columns of data in rows 7 and above. Column A contains donor numbers, column B contains the main variable in the testing methods (the blood collection tube type), Column C contains results of the tests for Sodium, Column D contains results of the tests for AST, and Column E contains results of the tests for Triglycerides. There were three types of blood collection tubes used in this study, Serum, SST™, and SST II™. As can further be observed from the exemplary table of Appendix A, specimens from 30 donors were tested, and each donor was tested for three analytes, Sodium, AST, and Triglycerides. For each donor, four blood specimens were drawn, two with the Serum type tube, and one each with the SST™ and SST II™ tubes, with each of the three analytes being measured in each specimen. Two specimens were drawn with the Serum tube, which in this case was considered to be the reference or control method. One specimen was drawn with each of the two evaluation devices. Thus there were twelve results (4 for each analyte) for each donor.

Tube type is the main variable in the exemplary test methods, but it should be understood that any variable could be evaluated, and blood collection tube type is chosen and discussed herein simply as an example. The serum tube was the reference or control device. The first evaluation device in this example was a blood collection tube labeled SST™, and the second evaluation device was a blood collection tube labeled SST II™.

Figure 2:
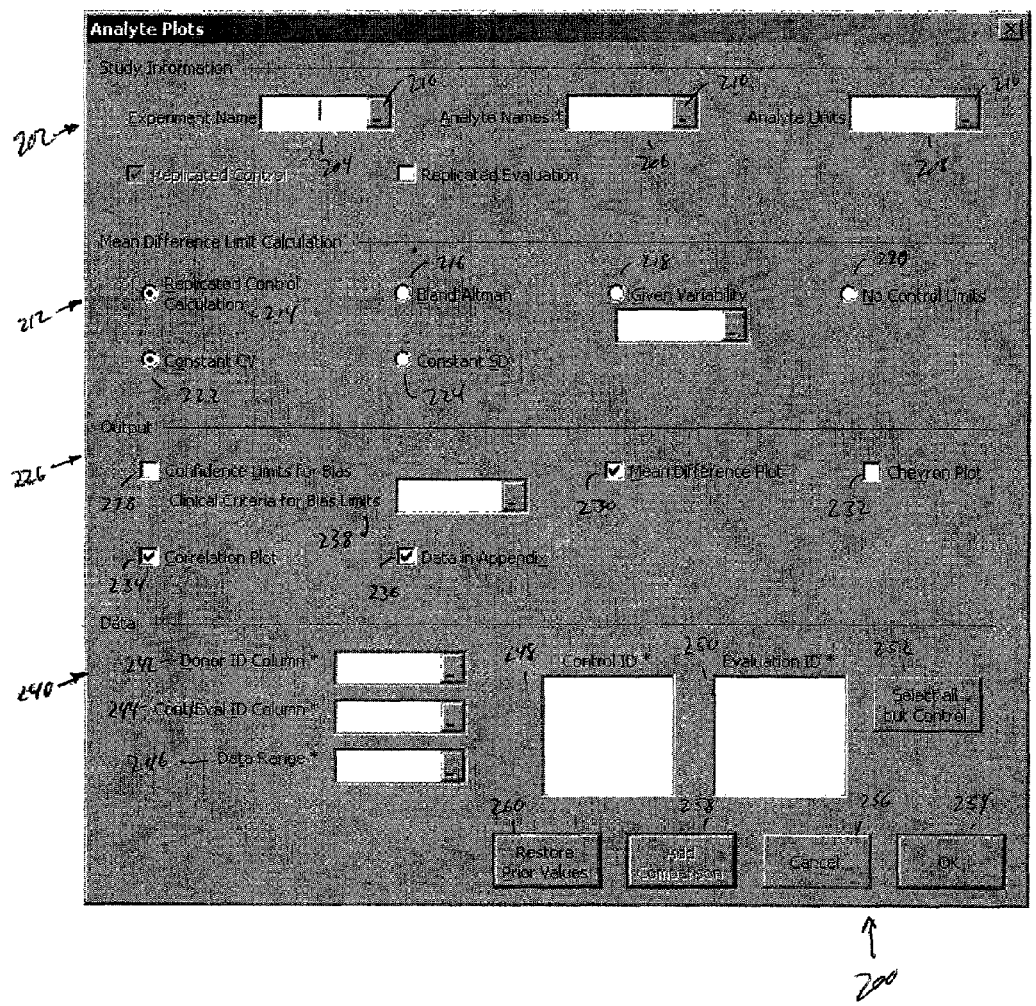
FIG. 2 is a screen shot representing a graphical user interface used to identify data in a spreadsheet representing reference and evaluation data in order to determine equivalence of testing methods.

The user interface will now be described in connection with FIG. 2, which is a screen shot of a user interface according to an embodiment of the invention. In the preferred embodiment of the invention, a graphical computer interface such as the one shown in FIG. 2 is provided. The invention is embodied in a computer program which acts as a plug-in to Microsoft® Excel. Of course it will be understood by those of skill in the art that the invention could be programmed as an independent software application running on a personal computer, or embedded in hardware, or implemented in any other suitable manner. When the plug-in is activated, the user interface 200 shown in FIG. 2 is presented.

The user interface 200 allows for the user to identify parts of a table, such as the spread sheet shown in Appendix A, which are related to reference and evaluation test methods, and to choose certain available options for the type of evaluation to be performed, as well as the types of outputs desired. The user then uses a mouse or other suitable input device to identify the corresponding portions of the table which contain the information needed by the program to perform the necessary calculations and generate the desired output.

For example, a portion of the user interface 200 is labeled "Study Information" 202. This portion includes Experiment Name 204, Analyte Names 206, and Analyte Units 208. The user has the option of typing the cell range corresponding to "Experiment Name" directly into the space provided for in the user interface at 204, or to click a button 210 allowing the user to use a mouse to identify the corresponding cell range within the Excel worksheet. Since the Experiment Name in this example is "Anaplot Test" at cell A6 of the table in Appendix A, cell A6 would be identified by the user in field 204 of the user interface. Similarly, cells C6-E6 would be identified as corresponding to the "Analyte Names" at 206 of the user interface 200. Cells C4-E4 would be identified as corresponding to "Analyte Units" 208 in the user interface 200.

A type of Mean Difference Limit Calculation is selected using the user interface 200 at 212. The choices are Replicated Control Calculation 214, Bland Altman 216, Given Variability 218, and No Control Limits 220. Only one of the four selection can be selected. Also, a choice between Constant CV 222 and Constant SD 224 is provided in this section 212. The types of Mean Difference Limit Calculations will be discussed in further detail below.

A portion of the user interface 200 is provided to allow for the selection of desired outputs 226. The possible selections preferably include Confidence Limits for Bias 228, Mean Difference Plot 230, Chevron Plot 232, Correlation Plot 234, and Data in Appendix 236. A checkbox for each type of output to be included is provided, and selecting any of the output types will cause the output to be included in the report generated by the system. The Clinical Criteria for Bias Limits 238 can also be set, either by entering the criteria directly in the space provided, or by referring to cells in a table which contain the clinical criteria for bias limits, such as an Excel worksheet.

A section of the interface 200 is provided for identifying certain relevant data 240. The data identified in this section includes a Donor ID Column 242, a Cont/Eval ID Column 244, and a Data Range 246. In the present example, Donor ID Column would refer to column A of the table reproduced in Appendix A. This is the column of data containing donor IDs. Cont/Eval ID Column 244 refers to the column in the table which contains the names of the reference and evaluation variables for each donor. In this example, column B of the table in Appendix A would be identified. Column B contains the labels for the blood collection tubes used in each test (Serum, SST™, and SST II™). The data to be evaluated, including reference data and evaluation data as appropriate, are identified in the Data Range 246 field. In this example, columns C, D, and E are identified as corresponding to the test results for both the reference and evaluation tests. These columns contain the actual test data for the three analytes tested, and for each of the 30 donors. The interface 200 also includes a field for Control ID 248 and Evaluation ID 250. A "Select All but Control" button 252 is provided. Finally, an "OK" button 254, a "cancel" button 256, an "add comparison" button 258 and a "restore prior values" button 260 are provided.

Figure 3:
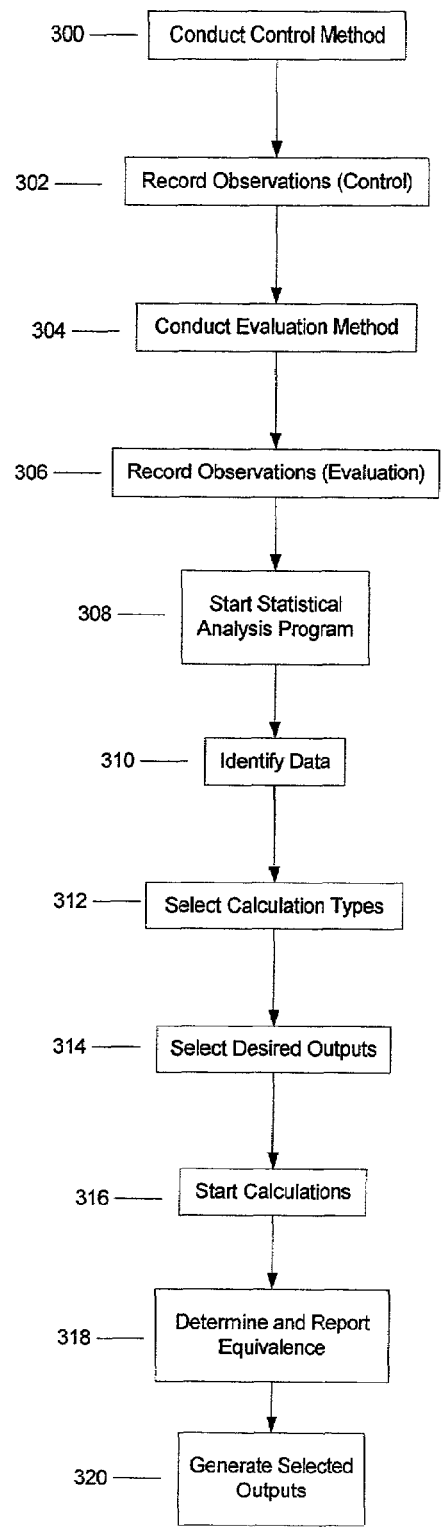
FIG. 3 is a flowchart illustrating a method according to an embodiment of the present invention.

The method according to an embodiment of the present invention will now be described in connection with the flowchart of FIG. 3. At step 300 a reference method is conducted. Observations from the reference method are recorded at 302. The reference method forms the basis for comparison to the evaluation method. Preferably, the reference method is performed at least twice, and observations of both reference methods are recorded. In this manner, the variability between successive runs of the same method can be measured. At step 304, the evaluation method is performed, and observations are recorded at 306. Preferably, the observations are recorded into a table, such as a Microsoft® Excel worksheet, to facilitate accessing the data for calculations to be performed by the statistical analysis program. More than one evaluation method may be performed and recorded. Advantageously, according to an embodiment of the present invention, any number of evaluation methods can be evaluated simultaneously.

At 308 the statistical analysis program is started. Preferably, this produces an interface as described above in connection with FIG. 2. Various data are identified in the user interface 200 at 310. Preferable, the data identified in the user interface 200 include the donor ID's associated with the data, the Control/Evaluation IDs, and the columns of data for the tests performed. A sample table of data is provided at Appendix A.

Also in the interface 200, the types of mean difference limit calculations desired are selected 312. The types available are Replicated Control Calculation 214, Bland Altman 216, Given Variability 218, and No Control Limits 220. Also to be selected are constant CV 222 or constant SD 224. If Replicated Control Calculation 214 is selected, the statistical program calculated the acceptable variability in the evaluation data based on the variability between the at least two sets of reference data. Bland Altman 216 selects a Bland Altman mean difference calculation. Given Variability 218 allows the user to select the acceptable variability. Finally, No Control Limits 220 allows the user to select a set of calculations without control limits.

At step 314, the user selects the desired set of outputs to be generated. These selections are available at 226 of the user interface 200. The user's choices comprise Confidence Limits for Bias 228, Mean Difference Plot 230, Chevron Plot 232, Correlation Plot 234, and Data in Appendix 236. Examples of each type of data will be described in greater detail below.

Once all data have been identified, and calculations and outputs have been selected, the user selects the "OK" button 254 at step 316 to begin the calculations selected.

A series of equations appropriate to the various selections available to the user are shown at Appendices B and C. Appendix B shows the set of equations associated with determining the slope and intercept in a correlation plot 234. Different equations are provided for different combinations of calculation type, and the kind and number of reference and evaluation data sets, as well as the type of variation selected. Appendix C shows the set of equations used to generate Chevron Plot data. The Chevron Plot will be described in greater detail below in connection with FIG. 4.

At step 318, the system determines based on statistical analysis, whether the evaluation data indicates that the evaluation method is clinically equivalent to the reference method or methods. Finally, at step 320 the selected outputs are generated, along with conclusions reporting whether the evaluation method is clinically equivalent or not.

Various outputs will now be described. The outputs described were based on the sample data provided in the table of Appendix A. A complete sample report is reproduced in Appendix D, and this report includes each of the types of outputs to be described in the foregoing description, for each of the three analytes tested in the reference and evaluation methods shown in Appendix A. For brevity, the outputs will each be described once in connection with one of the three analytes, AST.

Figure 4:
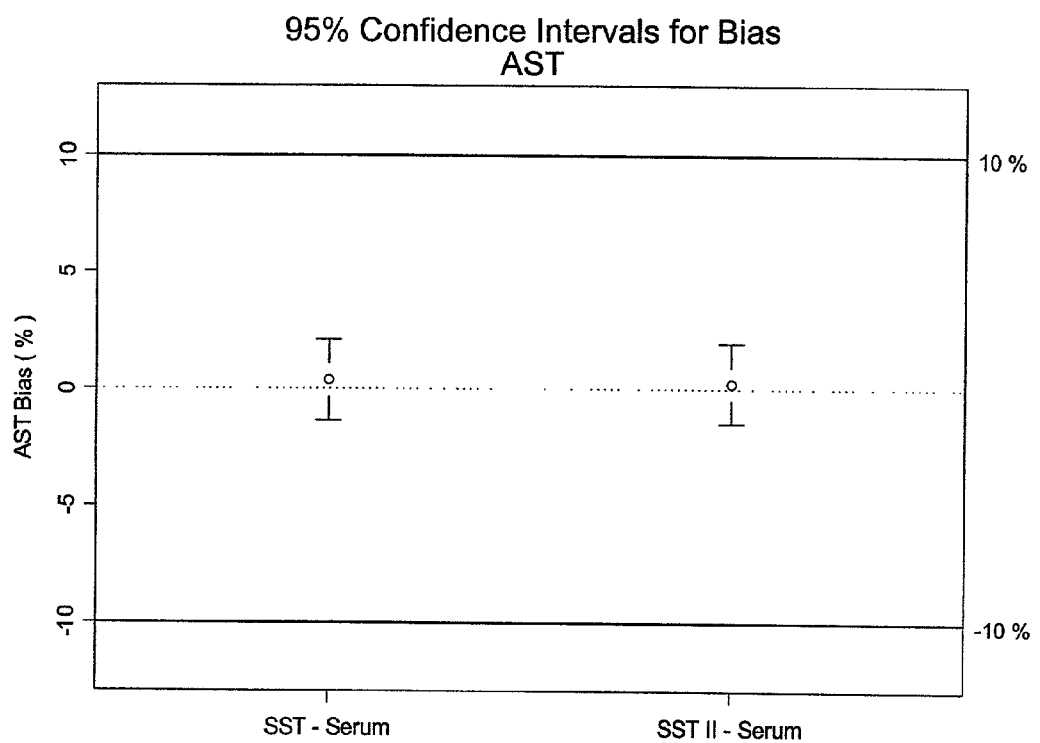
FIG. 4 is an optional output of the system, showing confidence intervals for two evaluation test methods.

FIG. 4 illustrates the Confidence Limits for Bias output, selected by checking Confidence Limits for Bias 228 in the user interface 200. The output shown in FIG. 4 corresponds to the analyte AST which was tested for each donor and for each reference and evaluation test method. The 95% confidence interval for bias gives a feasible range of possible values for the average bias or difference between results obtained using a reference method or device and an evaluation method or device. Thus, if the 95% confidence interval for bias in AST between SST™ and serum tubes is (5%, 8%), then there is 95% confidence that the true difference is somewhere between 5% and 8%. The confidence interval for each of the evaluation methods, SST™ and SST II™, are shown to be well within the 10% limits designated, indicating equivalence between the evaluation and reference devices.

Figure 5:
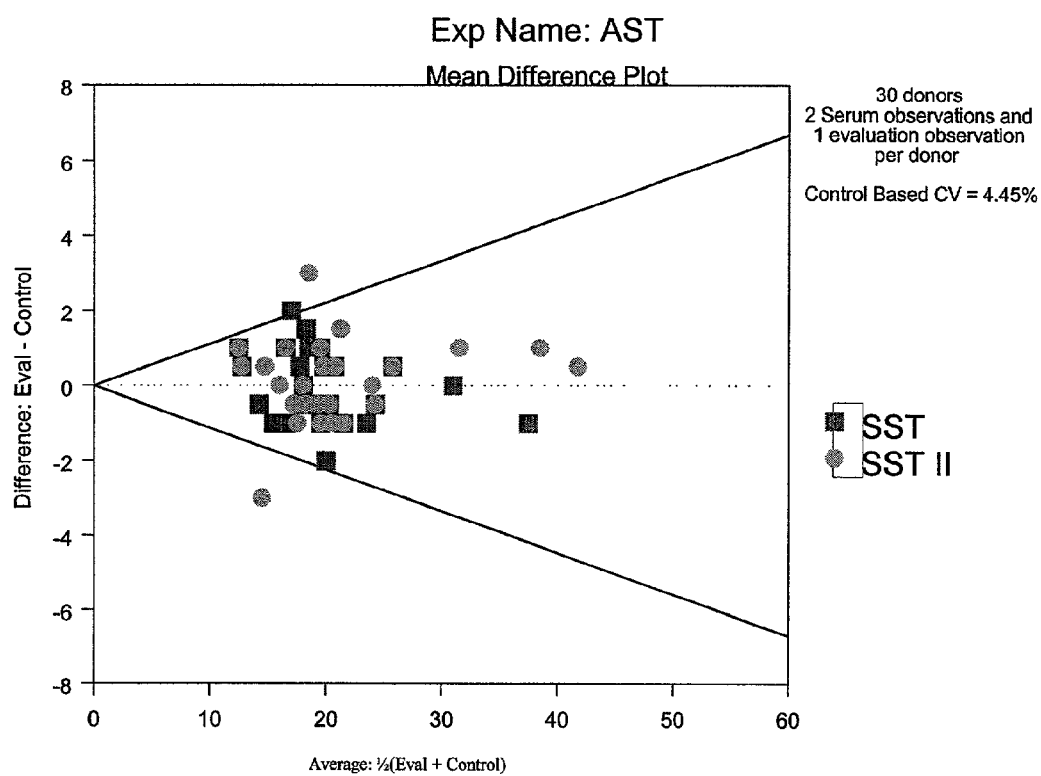
FIG. 5 is an optional output of the system, showing a mean difference plot for two evaluation test methods.

FIG. 5 illustrates a mean difference plot generated by the program according to an embodiment of the present invention. Data for each of the evaluation methods, SST™ and SST II™, are plotted. Each point represents a difference between the result observed using the reference method and the result observed using the evaluation method.

Figure 6:
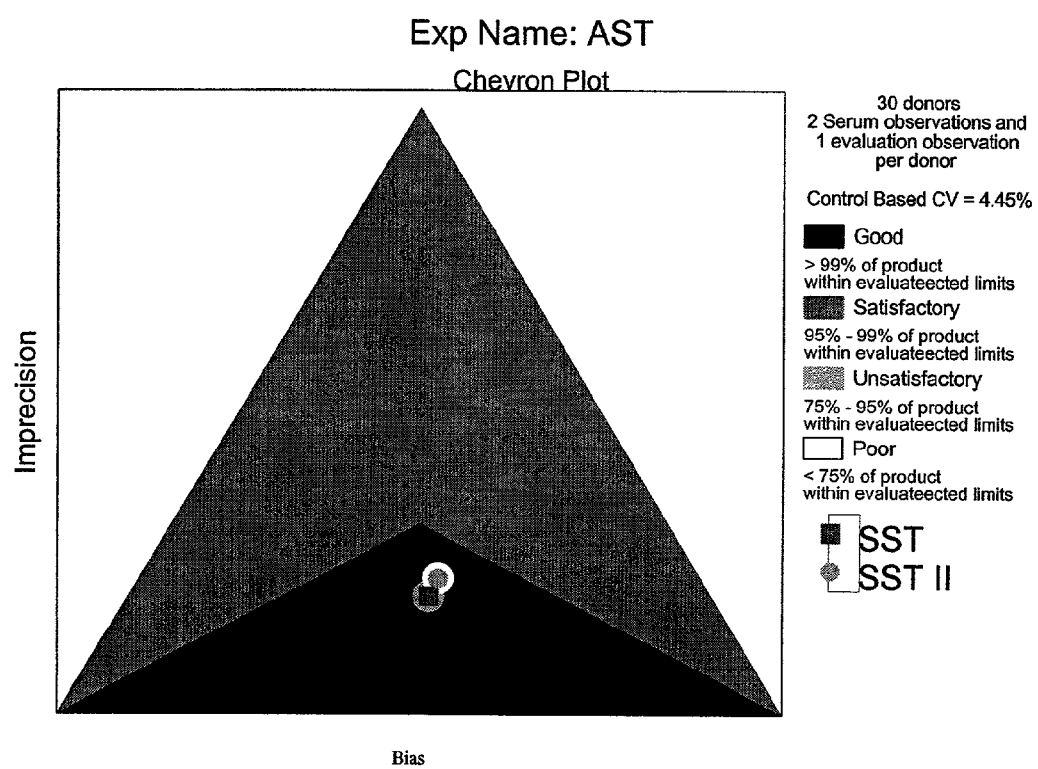
FIG. 6 is a variability chart generated by the system, showing accuracy of an evaluated test method on the horizontal axis and precision of the evaluated test method on the vertical axis.

FIG. 6 illustrates a Chevron Plot generated by the program according to an embodiment of the present invention. The Chevron Plot is a measure of bias (accuracy) and precision. Each evaluation experiment is plotted. Evaluation methods with a combination of good accuracy, and good precision are preferred. Regions are designated as "Good", "Satisfactory", "Unsatisfactory" and "Poor" so that the user can easily see which classification applies to each of the evaluation methods. Of course, it will be understood that while the Chevron Plot is the preferred manner of presenting accuracy and precision data, any graphical or non-graphical method of presenting accuracy and precision data is considered to be within the scope of the present invention.

Figure 7:
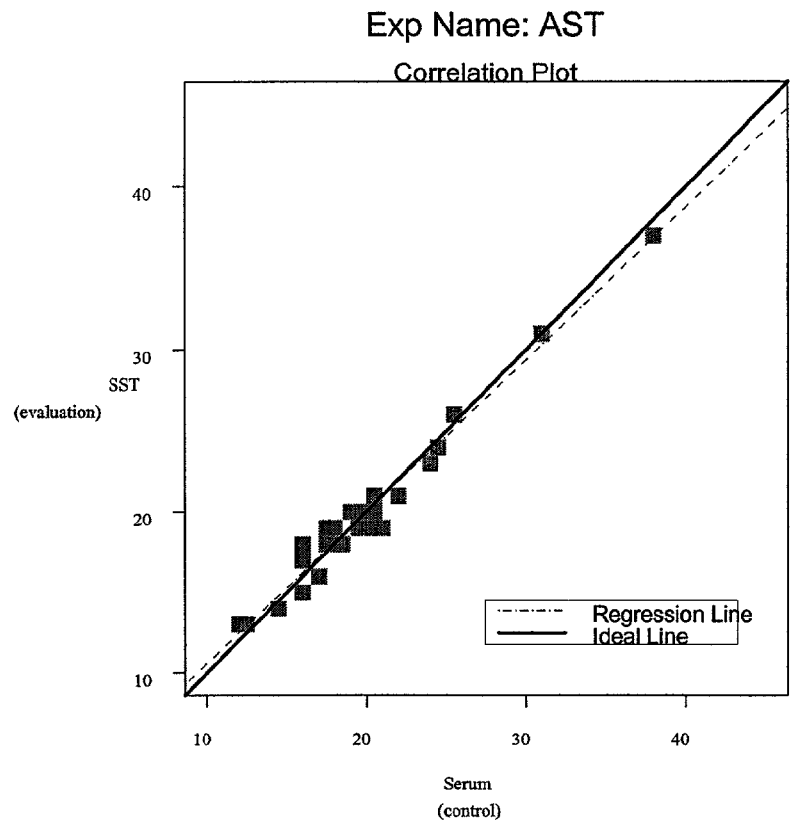
FIGS. 7 and 8 are correlation plots generated by a system according to an embodiment of the invention, illustrating the correlation between observations obtained using the evaluated test method and observations obtained using the reference test method.
Figure 8:
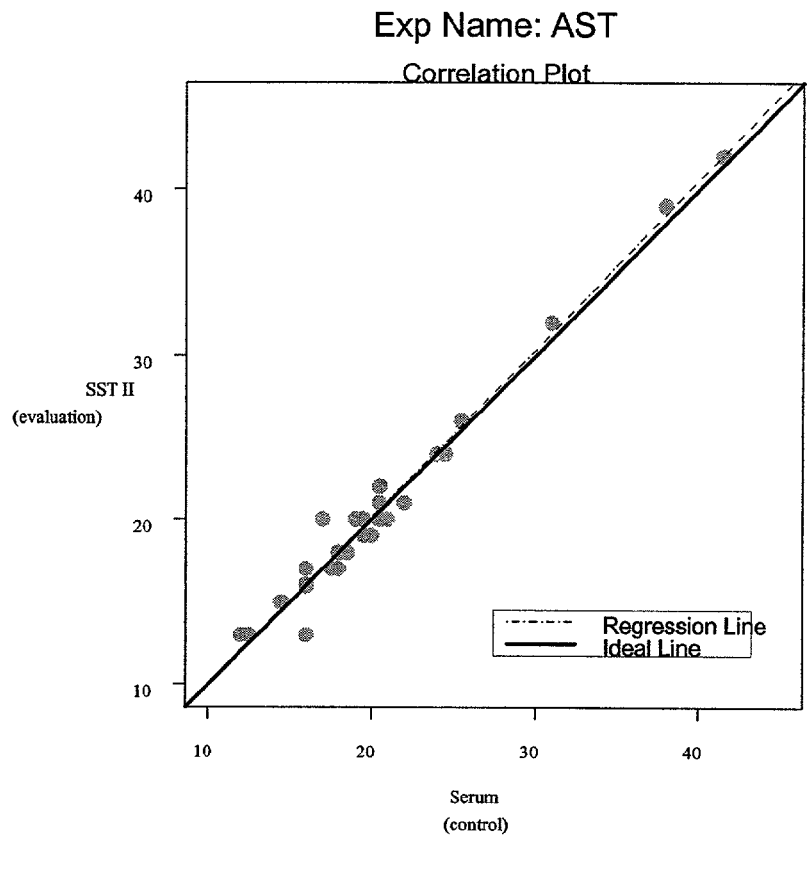

FIGS. 7 and 8 illustrate correlation plots generated according to an embodiment of the present invention. FIG. 7 correlates reference (Serum) results with the first evaluation method (SST™). FIG. 8 correlates reference results with the second evaluation method (SST II™). Regression is performed on the data and a regression line is plotted. An ideal line with slope equal to 1 and intercept equal to zero is also produced for comparison.

A sample report generated by the system according to an embodiment of the invention is reproduced in Appendix D. The report includes the various outputs selected in the user interface 200 as described above for each analyte tested. Also, the report includes conclusions about the clinical equivalence of the evaluation methods for each of the analytes evaluated. In this manner, new test methods (including existing test methods with new components, such as blood collection tubes, chemical reagents or analytical instruments), can be evaluated, and a lab can quickly and definitively determine that test results using the new method are clinically equivalent to previous test results. If the new method is shown not to be clinically equivalent, steps can be taken to correct the problem.

While the invention has been described by means of specific embodiments and applications, numerous modifications or variations could be made thereto by those skilled in the art without departing from the scope of the invention as set forth in the appended claims and equivalents thereof.

What is claimed is:

1. A method of determining whether an evaluation testing method is clinically equivalent to a reference testing method, comprising the steps of:
   determining a level of variance in results obtained using samples from each of a plurality of sources using a reference method,
   determining a standardized bias for the samples from each of the plurality of sources relative to the results from the reference method and the level of variance of the results from the reference method,
   obtaining an average bias from the standardized bias,
   determining a variability of the average bias from the standardized bias,
   iteratively computing a percentage of results from the evaluation testing method that occur within the variability of the reference method,
   concluding that the evaluation testing method is equivalent to the reference method if the computed percentage is 95% or greater, and
   generating a report including, in part, results of the reference method, results of the evaluation testing method, the average bias, the variability, and a conclusion of equivalence,
   wherein samples used in the reference method and samples used in the evaluation testing methods are from the same sources.

2. The method as claimed in claim 1, wherein said determining a level of variance in a reference method step comprises: computing measures of variability using at least two sets of reference test data associated with the reference method.

3. The method as claimed in claim 1, wherein said determining a level of variance in a reference method step comprises receiving user input representing the level of variance in the reference method.

4. The method as claimed in claim 1, wherein said report comprises a modified mean difference plot.

5. The method as claimed in claim 1, wherein said report comprises a linear regression analysis and a scatter diagram.

6. The method as claimed in claim 1, wherein said report comprises a variability chart having a first axis representing accuracy and a second axis representing precision.

7. The method as claimed in claim 1, wherein said report comprises a confidence interval for bias and a plot of the confidence interval.

8. The method as claimed in claim 1, further comprising the step of providing a graphical user interface for identifying data associated with the reference method and the evaluation testing method.

9. A system for determining whether an evaluation testing method is clinically equivalent to a reference testing method comprising:
   a memory adapted to store data related to samples from each of a plurality of sources, a reference testing method and an evaluation testing method, the data comprising, in part, test results;
   a processor adapted to:
      determine, from the data, a level of variance in results obtained from the samples using the reference method,
      determine a standardized bias for the samples from each of the plurality of sources relative to the results from the reference method and the level of variance of the results from the reference method, obtain an average bias from the standardized bias,
determine a variability of the average bias from the standardized bias,
iteratively compute a percentage of results from the evaluation testing method that occur within the variability of the reference method,
conclude that the evaluation testing method is equivalent to the reference method if the computed percentage is 95% or greater, and
generate a report including, in part, results of the reference method, results of the evaluation testing method, the average bias, the variability, and a conclusion of equivalence,
wherein samples used in the reference method and samples used in the evaluation testing methods are from the same sources.

10. The system as claimed in claim 9, wherein the data comprises at least two sets of reference data associated with the reference method.

11. The system as claimed in claim 9, wherein said system is adapted to receive user input representing the level of variance in the reference method.

12. The system as claimed in claim 9, wherein the report comprises a modified mean difference plot.

13. The system as claimed in claim 9, wherein the report comprises a variability chart having a first axis representing accuracy and a second axis representing precision.

14. The system as claimed in claim 9, further comprising a graphical user interface adapted to identify data in a table associated with the reference method and the evaluation testing method, respectively.

15. A computer readable medium of instructions adapted to control a system to determine whether an evaluation testing method is clinically equivalent to a reference testing method, comprising:
determining a standardized bias for the samples from each of the plurality of sources relative to the results from the reference method and the level of variance of the results from the reference method,
obtain an average bias from the standardized bias,
determine a variability of the average bias from the standardized bias,
iteratively compute a percentage of results from the evaluation testing method that occur within the variability of the reference method,
conclude that the evaluation testing method is equivalent to the reference method if the computed percentage is 95% or greater, and
generate a report including, in part, results of the reference method, results of the evaluation testing method, the average bias, the variability, and a conclusion of equivalence,
wherein samples used in the reference method and samples used in the evaluation testing methods are from the same sources.

16. The computer readable medium of instructions of claim 15, wherein the third set of instructions is further adapted to compare at least two sets of reference test data associated with the reference method to determine the level of variance in the reference method.

17. The computer readable medium of instructions of claim 15, wherein the third set of instructions is adapted to receive user input representing the level of variance in the reference method.

18. The computer readable medium of instructions of claim 15, wherein the fourth set of instructions is further adapted to generate a report including a modified mean difference plot.

19. The computer readable medium of instructions of claim 15, wherein the fourth set of instructions is further adapted to generate a report including a variability chart having a first axis representing accuracy and a second axis representing precision.

20. The computer readable medium of instructions of claim 15, further including a fifth set of instructions adapted to control the system to provide a graphical user interface adapted to identity data associated with the reference method and the evaluation testing method.

21. A method of determining whether an evaluation testing method is equivalent to a reference testing method, comprising the steps of:
determining a level of variance in results obtained using samples from each of a plurality of sources using the reference testing method;
determining a standardized bias for the samples from each of the plurality of sources relative to the results from the reference testing method and the level of variance of the results from the reference testing method;
obtaining an average bias from the standardized bias;
determining a variability of the average bias from the standardized bias;
iteratively computing a percentage of results from the evaluation testing method that occur within the variability of the reference testing method;
concluding that the evaluation testing method is equivalent to the reference testing method if the computed percentage is 95% or greater; and
generating a report comprising, in part, results of the reference testing method, results of the evaluation testing method, the average bias, the variability, and a conclusion of equivalence;
wherein samples for tests using the reference testing method and samples for corresponding tests using the evaluation testing methods are from the same sources.

22. A method of determining whether two testing methods are equivalent, comprising the steps of:
obtaining data corresponding to multiple samples from each of a plurality of sources and results from tests performed on the samples using at least two testing methods;
modeling the data as a function of the plurality of sources and the test results from the at least two testing methods;
extracting a bias, from the model, between a desired comparison of two testing methods selected from the at least two testing methods;
determining a variability of the extracted bias based, at least in part, on the model;
generating a confidence interval for the extracted bias;
comparing the confidence interval to a predetermined limit;
concluding that the two selected testing methods are equivalent if the confidence interval is within the predetermined limit; and
generating a report comprising, in part, results of the selected two testing methods, sources from which the samples were obtained, and a conclusion of equivalence.

23. A method of determining whether one or more evaluation testing method are clinically equivalent to a reference testing method, comprising the steps of:
obtaining at least two samples from each of a plurality of sources, at least one of the samples from each source being subjected to the reference testing method and at least one of the samples from each source being subjected to each of the evaluation testing methods;

obtaining data corresponding to the at least two samples, the plurality of sources, results from the reference testing method, and results from the one or more evaluation testing methods;

modeling the data as a function of the plurality of sources, the results from reference testing method, and the results from the one or more evaluation testing methods;

extracting a bias, from the model, between the reference testing method and each of the evaluation testing methods;

determining a variability of each extracted bias based, at least in part, on the model;

generating a confidence interval for each extracted bias;

comparing each confidence interval to a predetermined limit;

concluding that each of the evaluation testing methods is equivalent to the reference testing method if the confidence interval for a corresponding evaluation testing method is within the predetermined limit; and generating a report comprising, in part, results of the reference testing method, results of the one or more evaluation testing methods, the plurality of sources, and a conclusion of equivalence for each evaluation testing method.

* * * * *